United States Patent [19]

Daumas

[11] 3,996,273

[45] Dec. 7, 1976

[54] MANUFACTURE OF PHOSGENE FROM CHLORINE OBTAINED BY OXIDATION OF HYDROCHLORIC GAS AND FIXED ON REACTIONAL CHLORINE EXCHANGER MASSES

[75] Inventor: Jean-Claude Daumas, Orsay, France

[73] Assignee: Rhone-Progil, Paris, France

[22] Filed: Feb. 9, 1976

[21] Appl. No.: 656,144

Related U.S. Application Data

[60] Continuation of Ser. No. 445,539, Feb. 25, 1974, abandoned, which is a division of Ser. No. 268,750, July 3, 1972, abandoned.

[30] Foreign Application Priority Data

July 5, 1971 France ............................ 71.24449

[52] U.S. Cl. .......................................... 260/544 K

[51] Int. Cl.$^2$ .......................................... C07F 9/02

[58] Field of Search ................... 260/544 K, 544 M

[56] References Cited

UNITED STATES PATENTS

| | | | |
|---|---|---|---|
| 2,444,289 | 8/1945 | Gorin et al. | 260/544 K |
| 2,657,367 | 4/1972 | Blake et al. | 260/659 A |

*Primary Examiner*—Norman Morgenstern
*Attorney, Agent, or Firm*—McDougall, Hersh & Scott

[57] ABSTRACT

The manufacture of phosgene from carbon monoxide and chlorine obtained by oxidation of hydrochloric acid gas in which the chlorine is fixed in the form of a copper chloride on an exchange mass formed of a granular support of silica gel having a specific surface of 10 $m^2/g$ and a porous volume within the range of 0.3 to 1 cc/gram with the chlorides of potassium and copper being on the carrier with the possible addition of a chloride of rare earth metals.

3 Claims, No Drawings

MANUFACTURE OF PHOSGENE FROM CHLORINE OBTAINED BY OXIDATION OF HYDROCHLORIC GAS AND FIXED ON REACTIONAL CHLORINE EXCHANGER MASSES

This application is a continuation of application Ser No. 445,539, filed Feb. 25, 1974, which is a division of application Ser. No. 268,750, filed July 3, 1972, both now abandoned.

The present invention relates to the manufacture of phosgene from carbon monoxide and chlorine obtained by oxidation of hydrogen chloride in which the chlorine is fixed in the form of copper chloride on a reactive chlorine exchanger mass.

As is known, phosgeneous a compound frequently used in various organic chemical syntheses, such as in the synthesis of acid chlorides, chlorocarbonates and particularly isocyanates by reaction with amines. However, some of these syntheses, and particularly that of the isocyanates, lead to the necessary and simultaneous formation of hydrochloric acid gas, which represents a loss in chlorine in the absence of the ability to recycle the hydrogen chloride to the reaction for production of phosgene from carbon monoxide and chlorine.

Also, in order to avoid such losses, it has been proposed in the prior art, in a first phase, to oxidize the hydrochloric acid gas in the presence of masses containing cuprous chloride, possibly containing also an alkaline metal and, in a second phase, to have the cupric chloride so obtained react with carbon monoxide to manufacture phosgene. Such use of cuprous chloride, as a receiver of chlorine resulting from the oxidation of hydrochloric acid gas, has been well known for a long time and numerous formulae of diverse masses have been proposed, either for producing chlorine in elementary form or for use in the production of various chlorinated hydrocarbons where they function frequently as catalysts because it is possible to obtain these chlorinated hydrocarbons in a single phase, by contacting these masses containing cupric chloride with a gaseous mixture containing the hydrochloric acid gas, oxygen and the hydrocarbons to be chlorinated.

In the case of chlorination of carbon monoxide, it has been found that a single phase method cannot be used because of the ready hydrolysis of phosgene and due to the transformation reaction of carbon monoxide into carboxylic acid gas at the temperatures employed. When used in a two stage method, the masses containing copper chloride should be present in stoichiometric quantities and are not qualified as catalysts.

These types of prior methods for producing phosgene, use, as supports forming these masses, porous refractory oxides of various kinds and report rather low yields for rather high operating temperatures, which are likely to cause serious corrosion of the complex equipment. These different inconveniences are such as to prevent the method from being adopted industrially.

Experiments have shown that the indications previously furnished, on the makeup of these masses, were not sufficiently precise to obtain, in all cases, the announced yields which, incidentally, were insufficient from an industrial point of view and they show that the improvement of the results could be obtained only by precise selection of the nature and characteristics of the supports used in the preparation of these masses, the quantities of active elements employed, being a function of the porous characteristics of the supports.

More precisely, it has been found that use can be made of supports which are formed of porous silica gel granules having a specific surface of less than 10 $m^2/g$ with a porous volume within the range of 0.3 to 1 cc/gram; in which the active phase, at the end of the first stage, is constituted of cupric chloride and potassium chloride, the quantity of copper being from 10% to 20% by weight of the mass and the ratio of K/Cu, expressed in atoms, being between 0.2 and 0.4. It has been found moreover, that the addition of up to 4% by weight of rare earth metals in the form of their chlorides, makes it possible further to improve the already sufficient results capable of being achieved by the masses containing copper and potassium only in the active phase. Such masses allow for the realization of the previously described two step method for manufacturing phosgene, not only at temperatures lower than those previously indicated, but, what is more, they bring about a reduction in the transformation rate of carbon monoxide into carboxylic acid gas, as well as reducing the quantity of elementary chlorine by-product to a zero value.

The reasons for the superiority of the masses of this invention are not fully understood. It is believed, on the one hand, that the supports of different chemical nature, such as the supports formed of silica and magnesia or alumina, modify the state under which copper is present in the masses, portions of which convert to the oxychlorides or even the oxides, and that, on the other hand, supports of large surface area, regardless of their chemical nature, favor the transformation of carbon monoxide into carboxylic acid gas, as well as the hydrolysis of the phosgene, due to the possible retention of water, despite the removal with the aid of inert gases, between the first and second step of the method.

Industrially, it is feasible to employ the masses of the present invention in methods which make use of a fluid bed, mobile bed, or fixed bed reaction. However, it is preferable to use fluid or mobile beds, since they allow for the continuous operation of the method and because, particularly with respect to the highly exothermic first phase, they make it possible to maintain more precise operating temperatures. The use of pressure in both phases of the method, while not offering advantages from the standpoint of the reaction of carbon monoxide on cupric chloride, nevertheless favors the obtaining of greater contact times and a tendency of reducing the dissociation of the cupric chloride with the concomittent appearance of chlorine. Such pressure may be more or less elevated, but, for technological reasons, it is impractical to exceed approximately 10 bars.

The preparation of the different masses, in accordance with the practice of this invention, can be accomplished by any known means. In the preferred method, the silica gel supports are impregnated once or several times with solutions of metal chlorides in such quantities and concentrations that, after drying, the desired proportions of active elements are obtained, or by impregnation by means of compounds of these metals capable of furnishing the corresponding chloride during the first phase of the method.

Several comparative laboratory examples are hereinafter given which show the superiority of the masses embodying the features of this invention with masses of different supports. An example is also given for the fabrication of phosgene in a fluidized bed, in a pilot installation. All of the masses were obtained by impregnation of the selected supports with solutions of metal chlorides.

Because of the efficacy of the overall method, depending principally on the perfection of phase two, the comparative examples which show the superiority of the masses of this invention relate to said phase two. The masses indicated as the best in this phase were then verified as being suitable for phase one.

All of the laboratory tests of Examples 1 to 3 were carried out with a fixed bed in order to obtain sufficient contact time in a reactor having a diameter of 20 mm and a height of 100 mm maintained at the desired temperature by a tubular furnace. The reactor was fed either with a mixture of hydrochloric acid gas and air or with carbon monoxide, the outputs of which were measured with a rotameter. The reactor is provided with an analysis system, using chromatography, for controlling the $COCl_2$, CO, $CO_2$ and $Cl_2$ gases and a system for recovery of the phosgene that was formed, constituted by a trap containing caustic soda which, by giving the total chlorine, furnishes a second method for measuring the proportion of the chlorine initially present in the masses and fixed on the carbon monoxide in the phosgene state.

The different masses subjected to these tests, having a granulometry ranging from 80 to 200 microns, were first treated for three hours with a mixture of air and hydrochloric acid gas in a ratio of HCl : air = 0.7, at a temperature of 400° C. This makes certain that the copper is present entirely in the form of cupric chloride. Prior to the admission of the carbon monoxide, the treated masses are purged with nitrogen at a temperature of 350° C below the preceding temperature, in order to avoid chlorine losses. ,

EXAMPLE 1

The purpose of this example is to show the important part played by the specific surface of the silica support; the characteristics of the surface and the porosity of the different supports, the metal content of the different masses and the results are shown in the following table wherein $XCl_2$ designates the proportion of chlorine present in the masses, fixed on the carbon monoxide in the phosgene condition in two hours, XCO designates the proportion of carbon monoxide transferred in the sixth minute of operation, and % $CO_2$ is the proportion of $CO_2$ present in the gases after 30 minutes of operation; T is the temperature in ° C at which each experiment is conducted.

TABLE

| Characteristics of the supports and proportions of metals in the masses | | | | | | | |
|---|---|---|---|---|---|---|---|
| Specific Surface m²/grams | Porous Volume cc/gram | % Cu | K/Cu | T° C | $XCl_2$ | XCO | % $CO_2$ |
| 3.4 | 1 | 20 | 0.2 | 375 | 38 | 27 | 0.1 |
| 8 | 0.9 | 20 | 0.2 | 375 | 37.2 | 20.5 | 0.3 |
| 59 | 0.8 | 20 | 0.4 | 375 | 26.3 | 17.2 | 0.7 |
| 360 | 0.7 | 20 | 0.4 | 375 | 12 | 4.8 | 2.8 |

The effect of the specific surface is very clear from the values set forth in the above table. With a specific surface area above 8 m²/g, $Cl_2$ decreases more and more rapidly as well as the XCO, while the proportion of $CO_2$ formed increases.

EXAMPLE 2

The purpose of this example is to show the advantages resulting from using silica as support of the masses. These advantages result both from its chemical nature and its high porous volume. The porous volume is necessary in order to be able to impregnate the supports with optimum quantities of metal chlorides and to obtain masses having a porosity which is accessible to the reaction gases. Comparison is made of a mass supported on silica in accordance with the practice of this invention, although it is of little activity due to the relatively low copper content, with masses having supports of diverse porous characteristics formed of alumina or silica and magnesia. The proportions of metal chlorides are comparable.

The following table furnishes characteristics of the different supports and masses, the test temperatures as well as the results obtained, which are expressed in the same manner as in the preceding example.

TABLE

| Characteristics of the supports and proportions of metals in the masses | | | | | | | | |
|---|---|---|---|---|---|---|---|---|
| Support | Specific Surface m²/gram | Porous Volume cc/gram | % Cu | K/Cu | T° C | $XCl_2$ | XCO | % $CO_2$ |
| Silica | 8 | 0.9 | 10 | 0.3 | 375 | 32 | 8 | 0.1 |
| Alumina | 9 | 0.5 | 10 | 0.4 | 375 | 16 | 4 | 0.2 |
| Silica Magnesia | 9 | 0.3 | 10 | 0.4 | 375 | 10 | 2 | 0.2 |

The advantage of silica is clearly evidenced from the above. None of the other supports give equivalent results.

EXAMPLE 3

This example relates to the comparison between the results obtained on the same support with masses containing rare earth metals and a mass containing only copper and potassium, but prepared in accordance with the present invention. The characteristics of the masses and the results obtained, expressed in the same manner as in the previous examples, are shown in the following table, the support being silica having a specific surface of 3.4 m²/g and a porous volume of 1 cc/gram.

TABLE

| Proportion of metals in the masses | | | | | | |
|---|---|---|---|---|---|---|
| % of rare earth metals | % Cu | K/Cu | T° C | $XCl_2$ | XCO | % $CO_2$ |
| | | | 350 | 19.8 | 9.4 | |
| 3 | 20 | 0.2 | 375 | 31.6 | 13.0 | 0.1 |
| | | | 400 | 37.2 | 20 | |
| | | | 450 | 35.1 | 24.2 | |
| 4 | 10 | 0.2 | 375 | 34.4 | 9.0 | 0.1 |
| 4 | 10 | 0.4 | 375 | 31.4 | 11.1 | 0.1 |
| 0 | 10 | 0.2 | 375 | 31 | 8 | 0.1 |

This example clearly shows the superiority, at the same temperature, of the first three masses, particularly insofar as the proportion of transformed carbon monoxide is concerned.

EXAMPLE 4

This example relates to a pilot test, using a fluidized bed of a mass obtained by impregnation of silica microballs of 30 to 120 microns, having a specific surface of 8.4 $m^2/g$ and a porous volume of 1 cc/gram. The quantity of copper is 20% by weight of the finished mass, with copper being in the cupric form, and with the atomic ratio of K/Cu of 0.4. The overall equipment, in which the pressure is 5 bars, is constituted by:

a first stage reactor having a diameter of 500 mm, operating with a bed height of 9 meters, in which the contact time between the mass and the HCl:air mixture in a ratio of 0.5 is 30 seconds;

a second stage reactor having a diameter of 500 mm, operating with a bed height of 12 meters, and wherein the contact time between the carbon monoxide mass is 100 seconds.

The mass circulates between both reactors, the temperature of the first being 350° C and the second 375° C.

Under these conditions, the quantity of chlorine present in the gaseous circuit is maintained substantially zero, the conversion rate of the hydrochloric acid gas, in the first stage reactor, is substantially 100%, and that of carbon monoxide (XCO) in the second stage reactor is 30%.

This example shows, from the concrete results obtained, that the method of this invention is of an industrial character. This is due to the use of relatively simple equipment, while the methods described above, despite the use of much more complex equipment, does not give identical results, as a consequence of the use of masses with unspecified properties.

It will be understood that changes may be made in the details of formulation, construction and operation, without departing from the spirit of the invention, especially as defined in the following claims.

I claim:

1. The method for the preparation of phosgene comprising reacting hydrochloric acid gas, air and carbon monoxide in the presence of a reaction mass consisting essentially of a support containing copper chloride, potassium chloride, with or without a rare earth metal chloride, in which the support is formed of silica gel granules having a specific surface of less than 10 $m^2/g$ and a porous volume within the range of 0.3 to 1 cc/gram in which the amount of copper and rare earth metals are respectively within the range of 10–20% by weight copper and 0–4% by weight rare earth metals, the copper being present in the cupric state, the atomic ratio of K:Cu is within the range of 0.2–0.4, in which in a first phase the hydrochloric acid gas is oxidized in the presence of cuprous chloride to form cupric chloride and in which in a second phase the cupric chloride that is formed reacts with carbon monoxide to form phosgene.

2. The method as claimed in claim 1 in which the two stage reactions are carried out with the mass in a fluid or mobile bed.

3. The method as claimed in claim 1 in which the reaction mass is in a fixed bed.

* * * * *